United States Patent
Koshihara et al.

(10) Patent No.: US 8,466,673 B2
(45) Date of Patent: Jun. 18, 2013

(54) METHOD AND APPARATUS FOR DETECTING CONCAVO-CONVEX SHAPE SURFACE DEFECTS

(75) Inventors: Takahiro Koshihara, Tokyo (JP); Hiroharu Kato, Tokyo (JP); Akio Nagamune, Tokyo (JP)

(73) Assignee: JFE Steel Corporation (JP)

( * ) Notice: Subject to any disclaimer, the term of this patent is extended or adjusted under 35 U.S.C. 154(b) by 730 days.

(21) Appl. No.: 12/667,437

(22) PCT Filed: Aug. 20, 2008

(86) PCT No.: PCT/JP2008/065221
§ 371 (c)(1),
(2), (4) Date: Dec. 31, 2009

(87) PCT Pub. No.: WO2009/025384
PCT Pub. Date: Feb. 26, 2009

(65) Prior Publication Data
US 2011/0000338 A1  Jan. 6, 2011

(30) Foreign Application Priority Data
Aug. 23, 2007 (JP) .................... 2007-217180

(51) Int. Cl.
*G01N 27/82* (2006.01)
(52) U.S. Cl.
USPC .......................................... 324/238; 324/240
(58) Field of Classification Search
USPC ..................... 324/219, 228–229, 238, 240
See application file for complete search history.

(56) References Cited

U.S. PATENT DOCUMENTS

| 2,814,019 | A | * | 11/1957 | Bender ................. 324/221 |
| 3,535,625 | A | * | 10/1970 | Pratt ................... 324/233 |
| 7,417,425 | B2 | | 8/2008 | Machi et al. |
| 2002/0121896 | A1 | * | 9/2002 | Kato et al. ............. 324/232 |
| 2007/0108974 | A1 | | 5/2007 | Machi et al. |

FOREIGN PATENT DOCUMENTS

| JP | 58-086408 A | 5/1983 |
| JP | 5-256630 A | 10/1993 |
| JP | 6-058743 A | 3/1994 |
| JP | 8-160006 A | 6/1996 |
| JP | 2000-298102 A | 10/2000 |
| JP | 3271246 B2 | 4/2002 |
| JP | 2004-191220 A | 7/2004 |

(Continued)

OTHER PUBLICATIONS

Suechika et al, Partial Translation of JP 2004-191220 A, Aug. 7, 2004.*

(Continued)

*Primary Examiner* — Bot Ledynh
(74) *Attorney, Agent, or Firm* — DLA Piper LLP (US)

(57) ABSTRACT

A detection method for detecting a concavo-convex shape surface defect existing on a ferromagnetic metal object including sensing a signal attributed to strain of the concavo-convex shape surface defect having a size in a range of 0.5 to 6 μm. The signal is magnetic flux leaking from the ferromagnetic metal to which magnetic flux is applied. A detecting apparatus incorporates a magnetizer for magnetizing a ferromagnetic metal and a plurality of magnetic sensors arranged in the direction perpendicular to a traveling direction of the ferromagnetic metal to sense a signal attributed to strain of a concavo-convex shape surface defect having a size in a range of 0.5 to 6 μm.

16 Claims, 15 Drawing Sheets

FOREIGN PATENT DOCUMENTS

| | | |
|---|---|---|
| JP | 2005-061940 A | 3/2005 |
| JP | 2005-227133 A | 8/2005 |
| JP | 2007-071659 A | 3/2007 |

OTHER PUBLICATIONS

"Magnetic Flux Leakage Inspection Method for Iron and Steel Products," NDI Department (Technology and Technique Transfer Committee), Working Group for Quality Control, the Iron and Steel Institute of Japan, Feb. 28, 2001, pp. 144-147 and English translation (1 sheet).

Development of a Minute Inclusion Detector for Thin Steel Strips, CAMP-ISIJ, 1997, vol. No. 10, p. 289 and English translation (1 sheet).

"Development of Gouge Defect Detector," Chiba 2CGL, 131st Control Technology Working Group Meeting, Manufacturing Technology Department, the Iron and Steel Institute of Japan, Date, two-page coversheet and pp. 1-5 and partial English translation (1 sheet).

Yokota, H., "Development of Non-metallic Inclusion On-line Detection System," CAMP-ISIJ, 1994, vol. 7, p. 1270 and English translation (1 sheet).

Takada, H. et al., "State-of-the-art Techniques for Internal Quality Measurements in Steel Sheets Production Processes," Kawasaki Steel Giho, 1999, vol. 31, No. 4, pp. 211-215 (English Synopsis on first page).

"Report of Explorative Research on Seed Technology for Detection of Whetstone-inspection-level Flaws," Iron and Steel Technology Committee, the Japan Iron and Steel Federation, Jul. 1995, three-page coversheet and pp. 1-78 and partial English translation (1 sheet).

\* cited by examiner

BEFORE ANNEALING
RESULT OF STRAIN MEASUREMENT BASED ON X-RAY DIFFRACTION 0.00217

AFTER ANNEALING
RESULT OF STRAIN MEASUREMENT BASED ON X-RAY DIFFRACTION 0.00067

CONVEX DEFECT

CONCAVE DEFECT

STRONG MAGNETIZATION (48000 A/m)

WEAK MAGNETIZATION (8000 A/m)

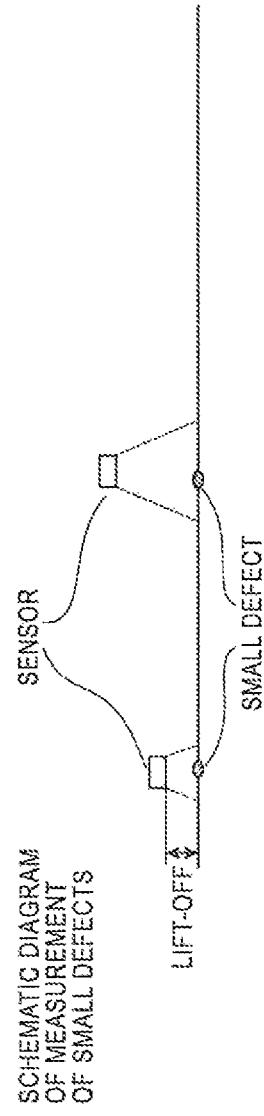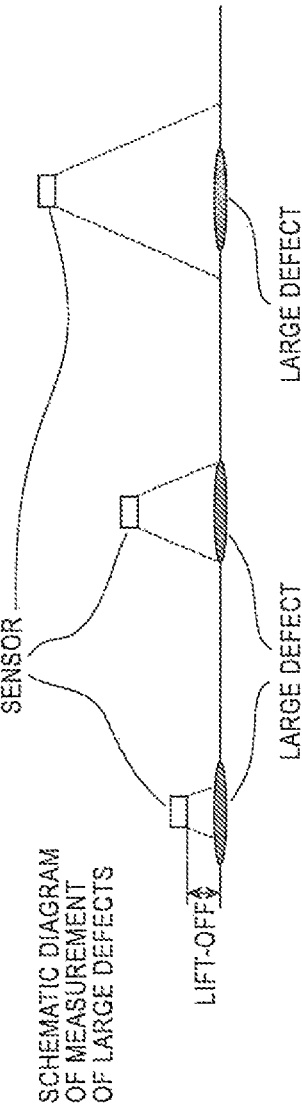

METHOD AND APPARATUS FOR DETECTING CONCAVO-CONVEX SHAPE SURFACE DEFECTS

RELATED APPLICATIONS

This is a §371 of International Application No. PCT/JP2008/065221, with an inter-national filing date of Aug. 20, 2008 (WO 2009/025384 A1, published Feb. 26, 2009), which is based on Japanese Patent Application No. 2007-217180, filed Aug. 23, 2007, the subject matter of which is incorporated by reference.

TECHNICAL FIELD

This disclosure relates to a method and an apparatus for detecting concavo-convex shape surface defects existing on a ferromagnetic metal and, in particular, to a method and an apparatus for detecting concavo-convex shape surface defects, wherein the concavo-convex shape surface defects each have a concavo-convex level in the range of 0.5 to 6 μm and an area of 10 mm² or larger and exist on a rough surface, with Ra being in the range of 0.5 to 2 μm, of a steel sheet having a thickness in the range of 0.4 to 2.3 mm.

BACKGROUND

In a manufacturing process of a ferromagnetic metal, in particular, thin steel sheets, foreign matter adhering to or caught up in a roll installed in a manufacturing line sometimes produces concavo-convex shape on the roll itself, and this concavo-convex shape may be transferred to resulting steel sheets as roll-generated flaws.

Such roll-generated defects include concavo-convex shape surface defects that each exist on a rough steel sheet surface (Ra=0.5 to 2 μm) and have a smooth outline (radius of curvature R≧10 mm), a concavo-convex level of 5 μm or lower, and an area of 10 mm² or larger. Such defects are hereinafter referred to as fine concavo-convex shape surface defects. FIG. 4 is a schematic diagram of a cross-section of a fine concavo-convex shape surface defect. The size of each fine concavo-convex shape surface defect is approximately in the range of 10 to 1000 mm² in area, but is 5 μm or lower in concavo-convex level as described above. The lowest concavo-convex level is approximately 1 μm, which is very small and is of the same order as the surface roughness.

Most of roll-generated defects have a relatively high concavo-convex level and are visible, and thus they can be easily found in the course of a manufacturing line. However, such fine concavo-convex shape surface defects have concavo-convex levels as small as the surface roughness of steel sheets. The optical difference between these fine defects and surface roughness is small, and thus the defects cannot be easily found in the course of a manufacturing line when observed without any treatment. However, once the surface is coated and the surface roughness is filled with a coating agent to make a smooth surface, the fine defects become clearly visible thereby posing serious problems in terms of appearance. Therefore, detection of fine concavo-convex shape surface defects prior to coating is an important issue in quality control.

The shape of fine concavo-convex shape surface defects includes point flaws like roll-generated flaws described earlier and flaws extending in the longitudinal direction of a steel sheet, such as linear marks or buckling marks.

Such fine concavo-convex shape surface defects are formed by transfer of concavo-convex shape of a roll to a steel sheet, and this situation persists until the roll is replaced or the process is improved. Therefore, early detection and countermeasures are very important also for yield improvement.

To find such fine concavo-convex shape surface defects, threading of steel sheets is stopped during operations in each inspection line in an iron-making process, and thereafter inspectors rasp all the coils with a whetstone and perform visual inspections thereof. After being rasped with a whetstone, convex portions, which are more strongly rasped than concave portions, have a higher reflectance than concave portions. This makes the difference between convex and concave portions clearer and more visible in visual inspections. This method is called whetstone inspection.

Unfortunately, this method necessitates stopping of inspection lines and requires a substantial period of time, thereby reducing the efficiency of operations. To address this situation, a method for automatically inspecting concavo-convex shape defects each having a concavo-convex level on the order of a few micrometers and a smooth outline has been developed. Examples of such an automatic surface analyzer may include the techniques disclosed in Japanese Unexamined Patent Application Publication Nos. S58-86408, H5-256630, H6-58743 and 2000-298102.

However, the technique disclosed in Japanese Unexamined Patent Application Publication No. S58-86408 is a technique for inspecting a mirror surface, and thus cannot be applied to an object with a large surface roughness because of the problem that beams converging into or diffused from concaves and convexes of flaws are masked by beams diffused by surface roughness and thus the flaws cannot be detected.

Also, the technique disclosed in Japanese Unexamined Patent Application Publication No. H5-256630 is intended for steel sheets, but still cannot be applied to objects other than materials having a mirror surface such as stainless steel sheets. Furthermore, this technique is admittedly effective in detecting concavo-convex defects extending perpendicular to the illumination detection, but is insufficient in terms of detection sensitivity for those extending parallel to the illumination detection.

Additionally, the technique disclosed in Japanese Unexamined Patent Application Publication No. H6-58743 is intended for unpolished wafers having rough surfaces, but still has the problem of low detection accuracy because it determines whether a flaw is present on the basis of the total light intensity and thus cannot detect specific signals of individual flaws.

The technique disclosed in Japanese Unexamined Patent Application Publication No. 2000-298102 was developed to address this situation and, accordingly, an apparatus for this technique has very high detection sensitivity. However, this technique requires an angle of incidence as large as close to 90°, thereby making it difficult to introduce a necessary apparatus into an actual operation line. It has also the problem that adjustment of optics is difficult.

In view of general defect-detecting methods without limiting the target thereof to fine concavo-convex shape surface defects, there are detection methods wherein magnetic flux is applied to a sample, for example, the technique disclosed in Japanese Unexamined Patent Application Publication No. H8-160006 for detecting an inclusion existing inside an object using a magnetic flux leakage inspection method. This patent document describes that surface defects can be detected also by using this magnetic flux leakage inspection method in the form of leakage flux signals generated by changes in the surface shape (signals generated by variation or disturbance of magnetic flux due to changes in the shape).

However, the intensity of signals for this magnetic flux leakage inspection corresponds to the shape change level of surface defects (concavo-convex change level), and thus the lowest shape change level of surface defects (concavo-convex change level) detectable in an automatic inspection is limited. Those skilled in the art consider this lower limit to be approximately 100 μm (Magnetic Flux Leakage Inspection Method for Iron and Steel Products, Feb. 28, 2001, NDI Department (Technology and Technique Transfer Committee), Working Group for Quality Control, the Iron and Steel Institute of Japan). In other words, it is recognized that stable detection of surface defects having a shape change level of approximately 100 μm or lower is difficult and signals generated by changes in the shape of approximately 100 μm or lower serve only as noise sources observed in flaw detection for other purposes (e.g., detection of inclusions).

Although such a simple comparison may be inapplicable, signals for detecting inclusions similarly correspond to the size of defects, and thus the lowest detectable size of a defect in the thickness direction of the test steel sheet is still limited. Those skilled in the art consider this lower limit to be approximately 10 μm (Development of a Minute Inclusion Detector for Thin Steel Strips, CAMP-ISU, Vol. 10 (1997)-289, Development of Gouge Defect Detector, Chiba 2CGL, 131st Control Technology Working Group Meeting, Manufacturing Technology Department, the Iron and Steel Institute of Japan, Development of Non-metallic Inclusion On-line Detection System, CAMP-ISIJ, Vol. 7 (1994)-1270 and State-of-the-art Techniques for Internal Quality Measurements in Steel Sheets Production Processes, Kawasaki Steel Giho, 31 1999 4.211-215).

Furthermore, in such magnetic flux leakage inspection, an increase in the sheet thickness would result in a widened range of flaw detection in the thickness direction, thereby resulting in increased background noise generated by the steel sheet, increased magnetizing force being needed for magnetization of the steel sheet, reduced flatness of the surface of the steel sheet leading to difficulty in scanning the steel sheet with a sensor, and other problems. For these reasons, the thicker the test sheet is, the more difficult flaw detection is. With the inclusion detector described in the publications listed above, the lowest detectable size of an inclusion in a steel sheet discussed, whose maximum thickness is 2.3 mm, would probably be much larger than 10 μm (size in the direction of the steel sheet thickness) if they can be detected at all, considering the fact that this inclusion detector is intended for thinner steel sheets used for cans.

Meanwhile, Report of Explorative Research on Seed Technology for Detection of Whetstone-inspection-level Flaws, July 1995, WG for research on cold rolling in rolling, refining, and temper systems, Iron and Steel Technology Committee, the Japan Iron and Steel Federation discloses the results of explorative research on the detection of whetstone-inspection-level flaws conducted by WG for research on cold rolling in rolling, refining, and temper systems, Iron and Steel Technology Committee, the Japan Iron and Steel Federation from September 1994 to July 1995 (Report of Explorative Research on Seed Technology for Detection of Whetstone-inspection-level Flaws). Previous approaches to automatic inspections of fine concavo-convex shape surface defects were mainly based on a light-detecting method, and, to date, there have been no approaches using a magnetic flux leakage inspection method.

Therefore, it can be said that the use of magnetic flux leakage inspection for detecting fine concavo-convex shape surface defects that can be visible only after the surface of a test steel sheet is rasped with a whetstone would not normally be considered by those skilled in the art of magnetic flux leakage inspection.

It could be helpful to provide a practical method for stable detection of concavo-convex shape surface defects that exist on a test object having a surface roughness Ra approximately in the range of 0.5 to 2 μm, wherein the concavo-convex shape surface defects are usually almost invisible and detectable only by whetstone inspection, are difficult to detect by automatic detection, and each have a concavo-convex level on the order of a few micrometers, and also provides an apparatus for the same objective.

SUMMARY

We thus provide:

[1] A detection method for detecting a concavo-convex shape surface defect existing on a ferromagnetic metal, including a step of sensing a signal attributed to strain of the concavo-convex shape surface defect having a size in a range of 0.5 to 6 μm.

[2] The detection method according to [1], wherein a thickness of the ferromagnetic metal is in a range of 0.4 to 2.3 mm.

[3] The detection method according to [1], wherein a ratio s/t of a size of the concavo-convex shape surface defect in a direction of a thickness s (μm) to the thickness of the ferromagnetic metal t (mm) is in a range of 0.63 to 9.0.

[4] The detection method according to [1], wherein the signal is magnetic flux leaking from the ferromagnetic metal to which magnetic flux is applied.

[5] The detection method according to [4], wherein a magnetic flux density of the ferromagnetic metal to which the magnetic flux is applied is at least 75% and lower than 95% of the magnetic flux density at magnetic saturation.

[6] The detection method according to [4], wherein the sensing is performed under combined conditions including a condition under which the magnetic flux density of the ferromagnetic metal to which the magnetic flux is applied is at least 75% and lower than 95% of the magnetic flux density at magnetic saturation and another condition under which it is at least 95% of the magnetic flux density at magnetic saturation.

[7] The detection Method according to [4], wherein the intensity of a magnetic field applied to the ferromagnetic metal is at least 4000 A/m and less than 25000 A/m.

[8] The detection method according to [4], wherein the sensing is performed under a combined condition obtained by combining a condition under which the intensity of a magnetic field applied to the ferromagnetic metal is at least 4000 A/m and less than 25000 A/m and another condition under which it is at least 25000 A/m.

[9] The detection method according to [1], wherein a distance between the ferromagnetic metal and a sensing apparatus that senses the signal is in a range of 0.5 to 1.5 mm.

[10] The detection method according to any one of [1] to [9], wherein the signal is a physical quantity attributed to strain of the concavo-convex shape surface defect occurring in a process that is a process downstream of rolling, which is a cause of the defect, and also is a process upstream of a process producing an annealing effect.

[11] The detection method according to any one of [1] to [9], wherein the signal is a physical quantity attributed to strain of the concavo-convex shape surface defect occurring in a process that is a process downstream of rolling, which is a cause of the defect, and comes later than temper rolling.

[12] A detection method for detecting a fine concavo-convex shape surface defect that has a concavo-convex level in a range of 0.5 to 6 μm and exists on a ferromagnetic metal sample including a step of detecting the surface defect by sensing a signal attributed to strain of a defect portion of the sample.

[13] A manufacturing method for manufacturing a ferromagnetic metal including the detection method according to any one of [1] to [9].

[14] A manufacturing method for manufacturing a ferromagnetic metal including the detection method according to [10].

[15] A manufacturing method for manufacturing a ferromagnetic metal including the detection method according to [11].

[16] A detecting apparatus for detecting a fine concavo-convex shape surface defect that has a concavo-convex level in a range of 0.5 to 6 μm and exists on a ferromagnetic metal sample, including means for detecting the surface defect by sensing a signal attributed to strain of a defect portion of the sample.

[17] A detecting apparatus for detecting a concavo-convex shape surface defect existing on a ferromagnetic metal, including a magnetizer for magnetizing the ferromagnetic metal and a plurality of magnetic sensors arranged in the direction perpendicular to a traveling direction of the ferromagnetic metal.

We provide for stable detection of fine concavo-convex shape surface defects that exist on a test object having considerable surface roughness, wherein the fine concavo-convex shape surface defects are usually almost invisible to the naked eye and detectable only by whetstone inspection, are difficult to detect in automatic detection, and each have a concavo-convex level on the order of a few micrometers and a smooth outline.

BRIEF DESCRIPTION OF THE DRAWINGS

FIG. 11 are schematic diagrams showing the situations of measurement of small and large defects.

DETAILED DESCRIPTION

Figure 1:
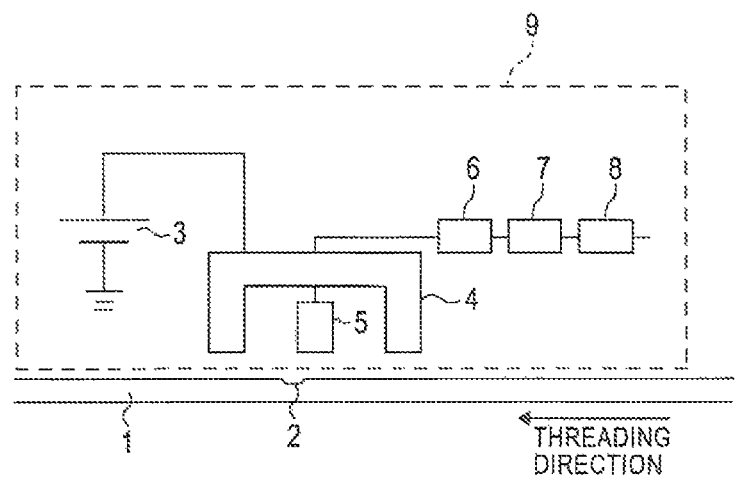
FIG. 1 is a diagram showing an illustrative configuration of our apparatus.
Figure 2A:
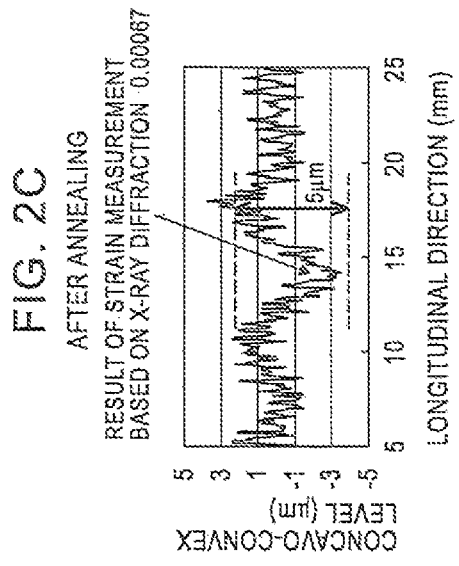
FIGS. 2A to 2D are diagrams showing example results of magnetic flux leakage inspection and shape measurement obtained before and after annealing.
Figure 2B:
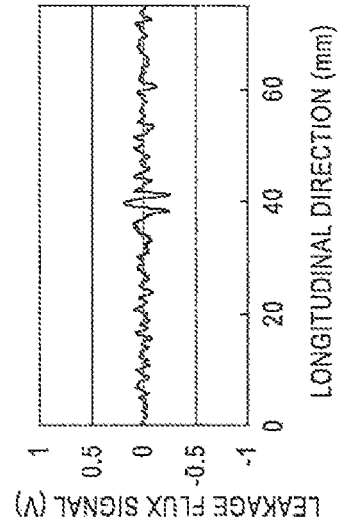
Figure 2C:
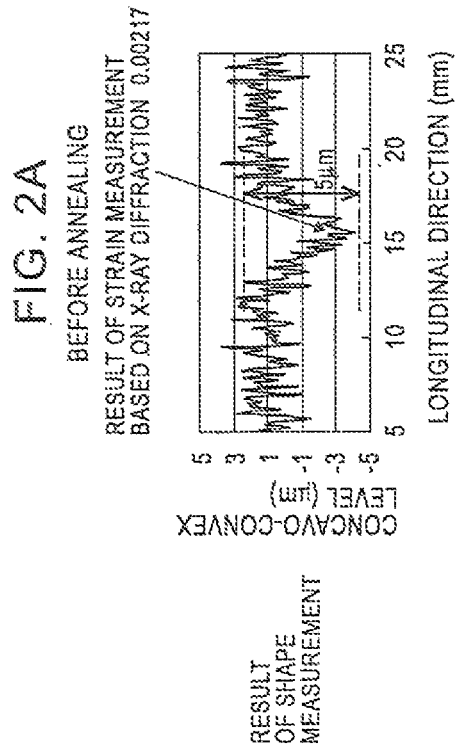
Figure 2D:
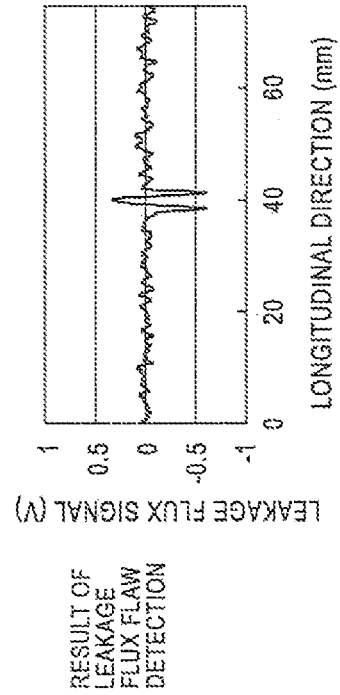

To measure fine concavo-convex shape surface defects generated during rolling (roll-generated fine concavo-convex shape surface defects), we first conducted X-ray diffraction analysis of such defects in some sheets to determine the physical characteristics of the defects. As a result, it was found that these fine concavo-convex shape surface defects had strain that probably emerged during transfer of flaws from the roll in the process of defect formation.

Therefore, we focused on the possibility that sensing signals attributed to the shape, which are insufficient for defect detection alone, together with such strain enables the detection of roll-generated fine concavo-convex shape surface defects and experimentally tested whether this strain generated during the formation of defects could be measured using a method based on magnetism. In this experiment, we first prepared a simple apparatus for magnetic flux leakage inspection, and then tried to detect roll-generated fine concavo-convex shape surface defects in some sheets to confirm that this apparatus could sense signals. After that, the samples were annealed at 850° C. for 10 minutes so that the strain thereof was fully removed, and then subjected to magnetic flux leakage inspection once again. As a result, it was found that the intensity of signals sensed after annealing was substantially lower than that sensed before annealing. FIG. 2 are diagrams showing example results of magnetic flux leakage inspection and shape measurement obtained before and after annealing.

The defect shown in FIG. 2 had a concavo-convex level of 5 μm, which was slightly larger than the minimum detectable size of a fine concavo-convex shape surface defect. FIGS. 2A and 2B represent the state before annealing, whereas FIGS. 2C and 2D represent the state after annealing. Also, FIGS. 2A and 2C represent the shape distribution in the longitudinal direction (traveling direction), whereas FIGS. 2B and 2D represent the values of signals sensed by the magnetic flux leakage inspection apparatus in the longitudinal direction (traveling direction). In the defect portion, the strain level measured using X-ray diffraction decreased from 0.00217 to 0.00067 during annealing. The results shown in FIGS. 2B and 2D also demonstrated that, in the defect portion, the leakage flux signal also decreased by half, from 0.85 to 0.41 V. Since this defect was slightly larger than the minimum detectable size, its leakage flux signal intensity reduced by approximately half was still detectable. However, it can be clearly seen in the drawings that this signal was significantly lowered by removing the strain.

Figure 3:
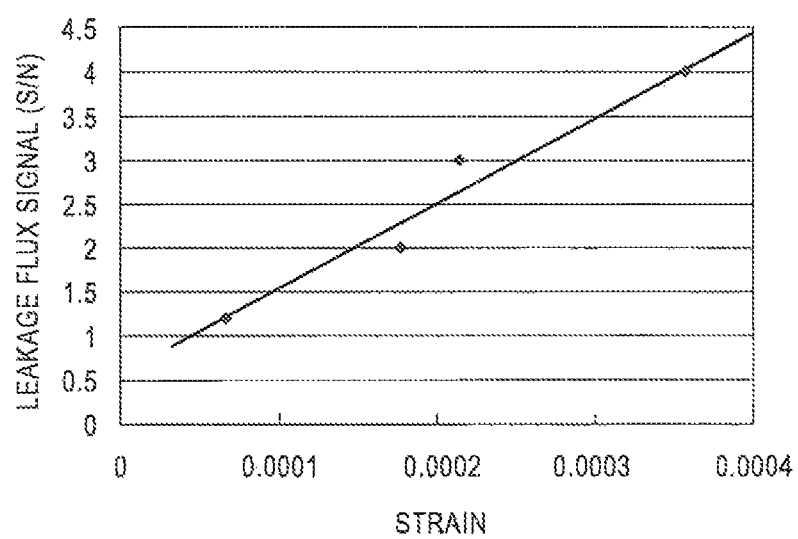
FIG. 3 is a diagram showing the relationship between strain and leakage flux.
Figure 4A:
FIGS. 4A and 4B are schematic diagrams each showing the cross-sectional shape of a concavo-convex shape surface defect.
Figure 4B:
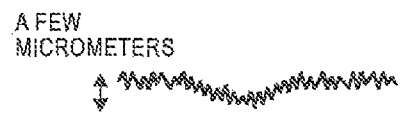

FIG. 3 is a diagram showing the relationship between strain and leakage flux, which was obtained by plotting the strain measured using X-ray diffraction in some roll-generated fine concavo-convex shape surface defects whose concavo-convex levels were almost identical against the results of magnetic flux leakage inspection. FIG. 3 demonstrates the strong relationship between the strain and the leakage flux signals, and this result also shows that the strain can be detected using leakage flux.

Consequently, we found that roll-generated fine concavo-convex shape surface defects cannot be detected only with signals attributed to the concavo-convex shape of such defects, whose concavo-convex levels are of the same order as the roughness. However, sensing signals of internal strain, which emerges during the formation of the roll-generated fine concavo-convex shape surface defects, together with the signals attributed to the concaves and convexes enables defect detection using a detection method based on magnetic flux (here, examples of such a detection method based on magnetic flux may include magnetic flux leakage inspection using direct current, magnetic flux leakage inspection using alternating current, eddy current inspection, residual magnetic flux inspection, and magnetic particle inspection). On the basis of these findings, we optimized various conditions to be suitable for the characteristics of such fine concavo-convex shape surface defects.

The principle of detection of strain in magnetic flux leakage inspection is described below. Strain generates leakage flux signals, and this is probably because strain changes the crystal lattice interval in the sample and accordingly changes the interaction between spins, thereby changing the magnetic characteristics of the sample. However, a usual magnetic flux leakage inspection method generally uses a saturated magnetic flux for measurement to improve the signal intensity and remove the influence of noise generated by unevenness of magnetic characteristics (magnetic permeability) of the test object.

If a sample is very strongly magnetized to magnetic saturation as with those used in such usual magnetic flux leakage inspection, spins are all aligned in the same direction and thus the signals of strain are probably suppressed. Therefore, a magnetization level that is lower than magnetic saturation (rotational magnetization region) is considered preferable because it results in stronger signals of strain. This probably corresponds to the fact that the comparison between the measurement data of the B-H curve obtained in a steel sheet strained over the entirety thereof by applying an external force thereto and that obtained in the steel sheet without any strain gives a larger difference in the region of magnetization levels lower than those in the magnetic saturation region (rotational magnetization region).

Therefore, the measurement of roll-generated fine concavo-convex shape surface defects involves measurement of signals attributed to strain, and sensitive measurement of such signals can be more easily achieved by using magnetization levels lower than saturated magnetization. It should be noted that the intensity of a magnetic field applied to a sample described herein means not the total magnetic field generated by a Magnetizer for magnetization of the sample, but also the magnetic field directly applied to the test site of the sample, i.e., the quantity corresponding to H in a B-H curve obtained in the test site of the sample.

Meanwhile, such a magnetic flux leakage inspection apparatus is usually used for product inspections in a final line, so that there are various processes between occurrences of defects and detection of them. These processes include, for example, a step wherein the steel sheet is released from strain, which emerges during the formation of defects, through the removal of the strain by heat, the release of strain by means of another stress such as tension applied during threading, or other circumstances. In such a process, detection of signals attributed to strain may be impossible. Therefore, the location where the detection is performed should be discussed.

Figure 8:
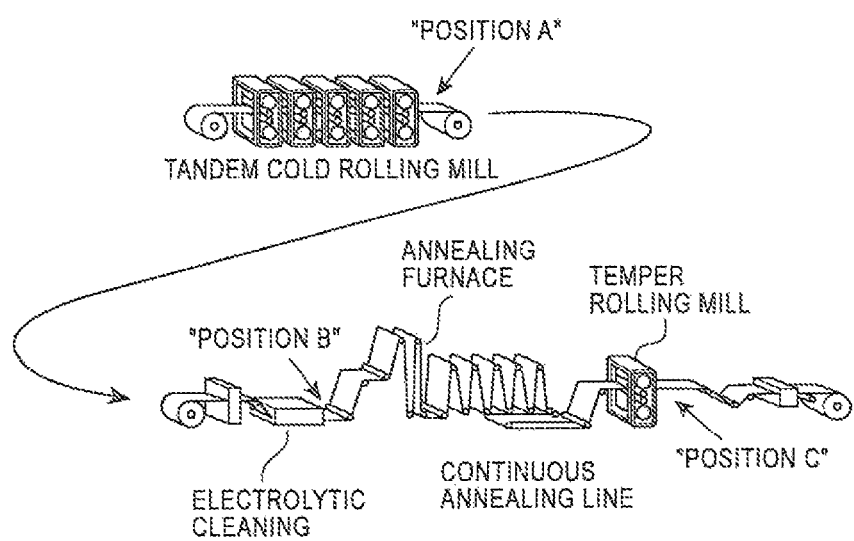
FIG. 8 is a schematic diagram of example manufacturing processes used for cold rolled steel sheets.

FIG. 8 is a schematic diagram of example manufacturing processes of cold rolled steel sheets. Major manufacturing processes of cold rolled steel sheets include cold rolling and subsequent annealing and temper rolling. In general, roll-generated fine concavo-convex shape surface defects are generated by a mill roll used for cold rolling, a roll installed in an annealing furnace for the annealing process subsequent to cold rolling, or a temper roll used after the annealing process.

Manufacturing processes of cold rolled steel sheets usually include a thermal process, such as an annealing process, to remove the influence of hardening that occurs during rolling. This thermal process sometimes involves a temperature increase to recrystallization temperature. Heating a steel sheet in this thermal process may result in the suppression of defect signals as with the experiment described earlier. Therefore, measurement should be carried out at a point just after rolling that causes defects, like "Position A" in FIG. 8, or at a point between rolling that causes defects and a thermal process that gives a sufficient amount of heat to release strain (a process producing an annealing effect), like "Position B."

Even after strain is removed once through such a thermal process, another strain is provided by temper rolling. Because of the size of strain given to defect portions is different from that given to normal portions. Therefore, detection of defects is possible even after the thermal process as long as it is carried out at a point after temper rolling, like "Position C" in FIG. 8.

For detection of defects generated by every roll that causes defects described above, a preferred point to carry out the measurement is a point after temper rolling. Furthermore, a point just after temper rolling, "Position C" in FIG. 8, is the most preferable because at this point feedback and location tracking in the event of defects are easy and the strain condition of a steel sheet may be changed before this point by tension applied while the sheet is threading through the manufacturing line.

It should be noted that a manufacturing process of surface-treated steel sheets, such as galvanized steel sheets and tinned steel sheets manufactured using CGL, EGL, or other lines, basically includes the same processes until temper rolling although the manufacturing process further includes a plating process or other surface treatment processes. Therefore, the preferred point of such measurement is the same as that described above.

Even if an annealing process (CAL) or a plating process (CGL, EGL) does not include temper rolling, the same result can be obtained by conducting such measurement at a point after tempering performed with a refining/temper line, such as a recoiling line.

In particular, in a plating process and later processes, defects that transfer concaves and convexes to the plated layer on the surface without affecting the substrate metal may occur. Such defects can be better detected after strain is given to the substrate metal by temper rolling, and thus a method wherein the measurement is carried out after temper rolling is especially preferable in this case.

Meanwhile, rolling at a high rolling reduction by rerolling or the like totally eliminates defects. Therefore, for successful detection of roller-generated defects, it is also obviously important to carry out the measurement between occurrences of the defects and rolling at a high rolling reduction. In addition, such rolling at a high rolling reduction admittedly eliminates defects totally; however, for the prevention of recurrences of defects, it is important to detect such defects also in the case that such rolling at a high rolling reduction is used.

Example

FIG. 1 is a diagram showing an illustrative configuration of an apparatus. In FIG. 1, 1 represents a steel sheet, 2 represents a roller-generated fine concavo-convex shape surface defect, 3 represents a direct current power source, 4 represents a magnetizer, 5 represents a magnetic sensor, 6 represents an amplifier, 7 represents a filter circuit, 8 represents a defect analyzer, and 9 represents a roller-generated fine concavo-convex shape surface defect detector.

The steel sheet 1 has a roller-generated fine concavo-convex shape surface defect 2 having a level in the thickness direction of a few micrometers, which is equivalent to the level of roughness. The roller-generated fine concavo-convex shape surface defect detector 9 is placed by the steel sheet 1, and the detector is configured as follows: the magnetizer 4 and the magnetic sensor 5 are arranged on the same side facing the steel sheet 1; the magnetizer 4 magnetizes the steel sheet 1 using direct current supplied by the magnetization power source 3.

Magnetic flux generated between both magnetic poles by the magnetizer 4 passes through the steel sheet 1. If a defect 2 exists on the steel sheet 1, strain that emerges during the formation of the defect 2 and surrounds the defect 2 interrupts the magnetic flux, and then the change in the magnetic flux can be detected by the magnetic sensor 5. The signal output from the magnetic sensor 5 is amplified by the amplifier 6, and then noise contained therein is removed by the filter circuit 7. After that, the defect analyzer 8 determines the point that corresponds to a signal having intensity equal to or higher than a threshold value to be a defect.

Although this example uses a direct current signal for magnetic flux leakage inspection, an alternating current signal may be used instead. In this case, a synchronous detection circuit is required. Furthermore, in this example, the magnetizer and the magnetic sensor are arranged on the same side facing the steel sheet. However, if a direct current signal is used, they may be arranged on opposite sides across the steel sheet, and even if an alternating current is used, they may be arranged in the same way, on opposite sides across the steel sheet, as long as the excitation frequency is sufficiently low for the sheet thickness.

In addition, although the defect analyzer 9 uses the intensity of a signal attributed to a defect for determination of the defect, the length, width, or area of a point that gives a signal having an intensity equal to or higher than a threshold value may be used for determination together with the signal intensity, and two or more of them may also be used in combination for determination. Also, the phase of alternating current may be used for determination in the case where alternating current is used.

Figure 7:
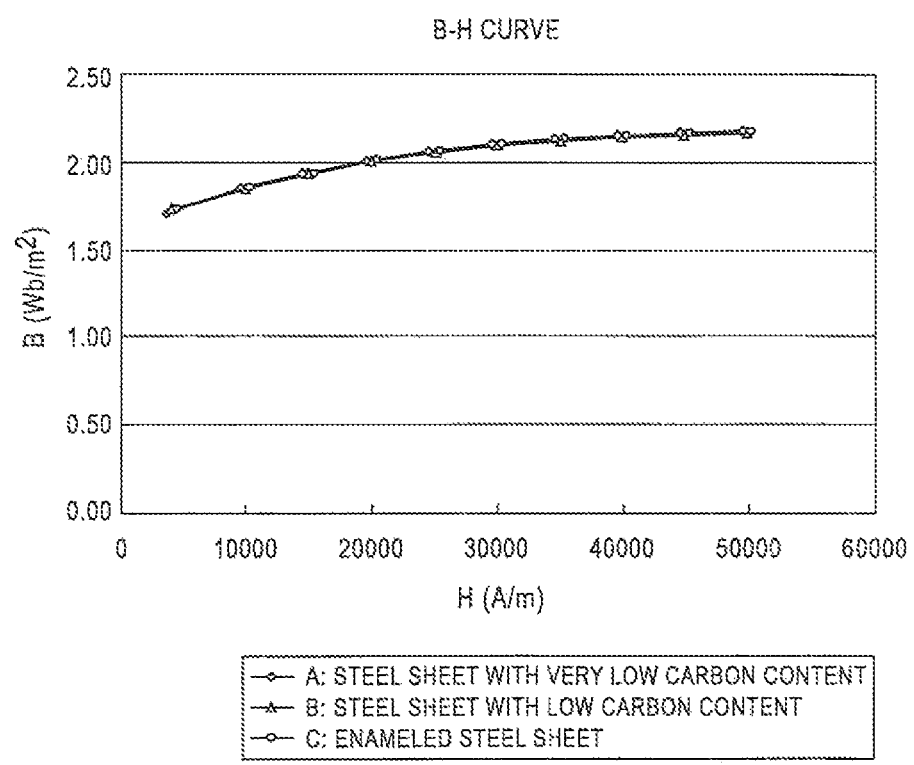
FIG. 7 is a diagram showing B-H curves obtained for three steels with different C %.

We measured B-H curves for some steels with different compositions. The result is shown in FIG. 7. This drawing includes B-H curves obtained for three steels with different C %, and A represents steel with very low carbon content (C %: 0.0 to 0.002), B represents steel with low carbon content (C %: 0.03 to 0.06), and C represents enameled steel (C %: approximately 0.0009). From the results, no difference due to the kind of steel was observed between B-H curves. After that, we examined these steels for roll-generated fine concavo-convex shape surface defects. A representative result (very low carbon content) is described below.

Figure 5A:
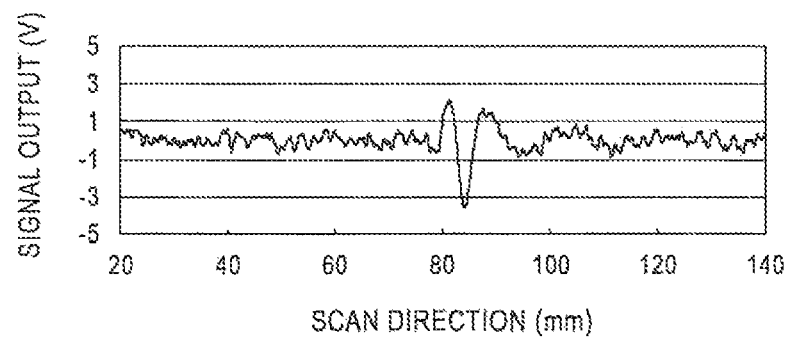
FIG. 5 are diagrams showing a comparison between a strong magnetization condition and a weak magnetization condition.
Figure 5B:
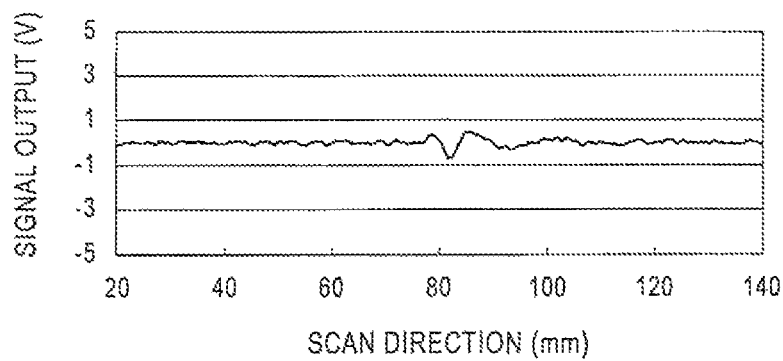

FIG. 5 are diagrams showing a comparison between a strong magnetization condition and a weak magnetization condition, and represent examples of flaw detection for roll-generated fine concavo-convex shape surface defects under the strong magnetization condition (48000 A/m) and the weak magnetization condition (8000 A/m). It can be seen that the signal intensity was reduced. Similar measurement was repeated with different magnetic field intensities, and the obtained signal level, noise level, and S/N were plotted against the magnetic field intensity, as shown in FIG. 6.

Figure 6:
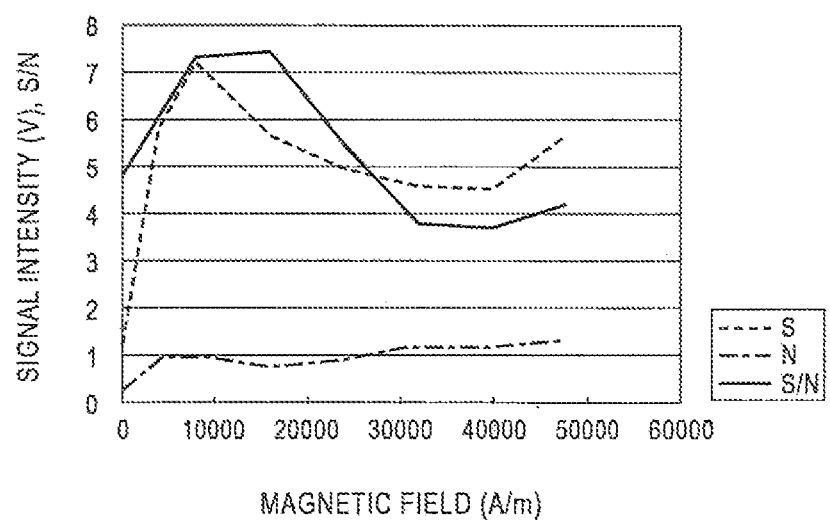
FIG. 6 is a diagram showing the relationships among the magnetic field intensity, signal level, and S/N.

As can be seen in FIG. 6, a magnetic field of at least 4000 A/m and less than 25000 A/m gave as high S/N as 5 or higher, and thus is suitable for detection. When applied to steel, this magnetic field has a magnetic flux density corresponding to 75 to 95% of that in the saturated magnetization state, as shown in FIG. 7.

Furthermore, as shown in FIG. 6, a magnetic field of 25000 A/m or higher, in particular, higher than 40000 A/m, resulted in an increased signal intensity (however, the noise level also increased and thus an increase in S/N was slight). This is probably because the signal component attributed to concaves and convexes of defects was increased. For measurement of such signals attributed to concaves and convexes of defects, conventionally used measurement at the saturated magnetization level is preferable. Here, the magnetic flux density resulting in a magnetic field of 25000 A/m or higher corresponds to 95% or higher of that in the saturated magnetization state as shown in FIG. 7. In particular, 40000 A/m or higher corresponds to 99%.

Also in detection of roll-generated fine concavo-convex shape surface defects, concaves and convexes are present although they are as fine as a few micrometers at minimum, and thus such signals attributed to concaves and convexes can be obtained as well. Therefore, the following two conditions for flaw detection can be combined to improve the sensitivity for detecting defects: flaw detection at a magnetic field intensity less than 25000 A/m for sensing signals attributed to strain; flaw detection at a magnetic field intensity of 25000 A/m or higher for sensing signals attributed to concaves and convexes. Furthermore, comparing the signal component attributed to concaves and convexes with that attributed to strain enables comparing of the concavo-convex level and the strain level, thereby making it possible to identify which roll causes defects by, for example, assuming that the combination of a low concavo-convex level and large strain represents a defect caused by a roll used at a high rolling reduction.

Meanwhile, in this example, the value of magnetic flux density was calculated from a magnetic field intensity on the basis of a predetermined B-H curve. The value of a magnetic field intensity for this calculation may be measured in the vicinity of the test site of a sample.

Although this example used leakage flux based on direct current for measurement, a leakage flux method based on alternating current, an eddy current inspection method, or a magnetic particle inspection method may be used instead as long as the method allows for sensing of signals attributed to strain.

Furthermore, although this example used a hall element as the magnetic sensor, a coil, a magnetic resistance element, or a SQUID may be used instead as long as the element can sense magnetism. Also, a single magnetic sensor or a plurality of magnetic sensors may be used. If plurality of magnetic sensors are used, a wider area can be simultaneously measured by arranging the magnetic sensors in the direction perpendicular to the traveling direction of the sample and parallel to the sample itself. However, a too large pitch of magnetic sensors would cause overlooking of defects passing between the magnetic sensors, whereas a too small pitch would reduce the efficiency. Although a pitch of magnetic sensors in the range of 0.5 to 3 mm is enough for detection, one in the range of 0.8 to 2 mm is the most preferable for sufficient detection sensitivity and efficiency.

Moreover, the lift-off used in this example was 1 mm, and this value was chosen on the basis of the following findings. Especially small ones of roll-generated fine concavo-convex shape surface defects sometimes give very slight leakage flux signals. To detect such defects, optimization of the lift-off, which is a distance between a sensor and a sample, is required in addition to the measures described earlier.

In general, defects necessitating whetstone inspection for detection thereof in an iron and steel manufacturing line are, as described earlier, those each having concaves and convexes equivalent to roughness (approximately a few micrometers) and a radius of curvature R of 10 mm or larger and thus masked by roughness of a few micrometers. Such defects often each have a diameter approximately in the range of 4 to 30 mm and an area approximately in the range of 10 to 1000 mm$^2$ on the surface of a steel sheet. In a usual magnetic flux leakage inspection method, a smaller lift-off results in a higher sensitivity and thus is more advantageous. However, in detection of such a defect, which has a concavo-convex level as small as a few micrometers and a large area, a too small lift-off would lead to the situation that only signals from a small portion of the defect are sensed, thereby posing a problem of poor efficiency in detection of defects, for example, the need for arrangement of a plurality of sensors.

Figure 9:
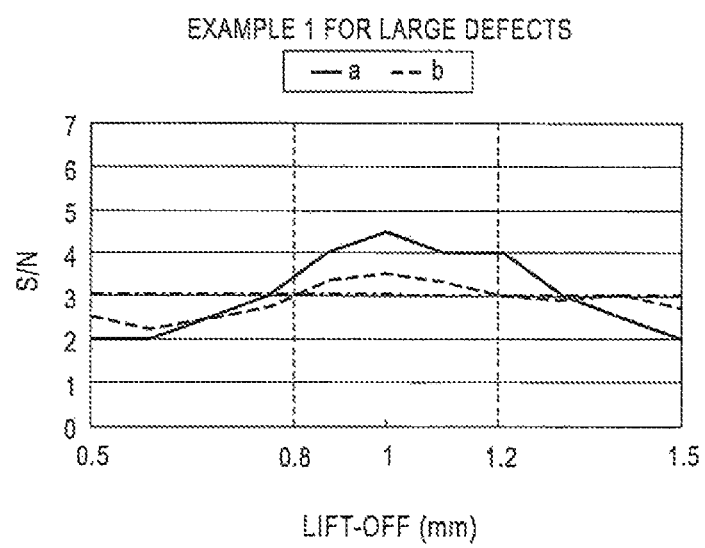
FIG. 9 is a diagram showing Example Relationship 1 between the lift-off and S/N.
Figure 10:
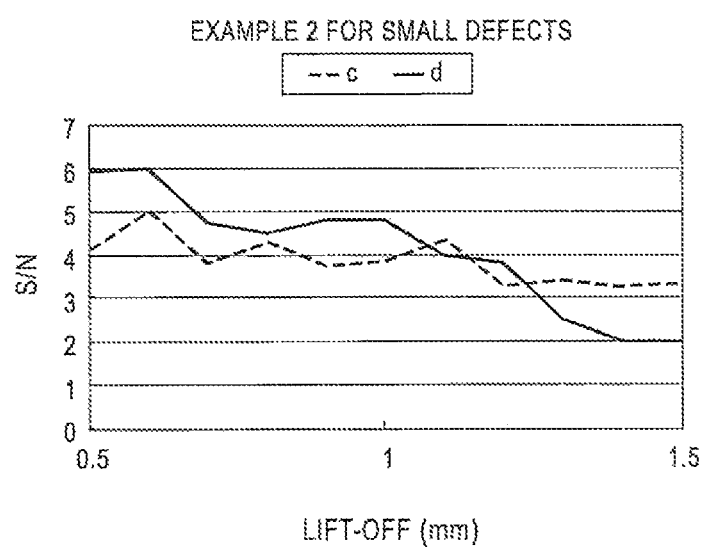
FIG. 10 is a diagram showing Example Relationship 2 between the lift-off and S/N.

FIG. 9 is a diagram showing Example Relationship 1 between the lift-off and S/N, and FIG. 10 is a diagram showing Example Relationship 2 between the lift-off and S/N. Each of these drawings is a graph made for the purpose of studying the relationship between the lift-off and S/N. FIG. 9 shows the results obtained by measuring the following sample defects each having a relatively small concavo-convex level of a few micrometers and a large area using different lift-offs: Sample a: 15 mm in length, 4 mm in width; Sample b: 10 mm in length, 4 mm in width. On the other hand, FIG. 10 shows the results obtained by measuring the following sample defects each having a relatively large concavo-convex level of a few tens of micrometers and a small area: Sample c: 1 mm in length, 2 mm in width; Sample d: 1 mm in length, 2 mm in width. In the example described above, a hall element with the area of magnetism-sensing portion being approximately 0.2 mm or smaller in diameter was used as the sensor.

In detection of small defects, the results of which are shown in FIG. 10, the conventionally known tendency in S/N to increase as the lift-off is decreased was confirmed. However, in detection of large defects (corresponding to an area of 5 mm or larger in diameter on the basis of the effective diameter of the defects a and b described above), the results of which are shown in FIG. 9, a tendency in S/N to reach its maximum at a lift-off of approximately 1 mm was observed. In addition, a lift-off in the range of 0.5 to 1.5 mm gave S/N of 2 or higher and thus is sufficient to be used for detection. However, considering the long and short dashed line representing S/N of 3, the level allowing for automatic detection, a preferred lift-off range for automatic detection is 0.8 to 1.2 mm. A lift-off of 1 mm gave especially high S/N and this suggests that the most preferred lift-off range is 0.9 to 1.1 mm.

This situation is discussed below with reference to FIG. 11. FIG. 11 are schematic diagrams showing the situations of measurement of small defects (corresponding to the defects c and d described above) and large defects (corresponding to the defects a and b described above).

It is generally known that, in magnetic flux leakage inspection, the leakage flux density coming from a defect increases as the detecting apparatus comes closer to a sample, and thus a smaller lift-off results in a stronger defect signal being detected, whereas a larger lift-off results in a weaker defect signal being detected. Another consideration is that the detection area detected by the sensor is widened as the lift-off is increased.

In general, a defect difficult to detect is one having small concaves and convexes and a small area. Such a defect is inherently smaller than the detection area of a sensor, and thus the area of the defect encompassed in the detection area of the sensor decreases as the lift-off is increased (see FIG. 11A). Here, signals existing in the detection area are averaged during detection, and thus the defect signals are averaged together with signals coming from the surrounding normal portion (background noise signals). Therefore, the signal intensity is further lowered. On the other hand, signals coming from such a normal portion have almost identical intensities, and thus a decrease in these signals is smaller than that in defect signals. Therefore, in detection of small defects, a decrease in the defect signal is larger than that in noise due to a sample itself, and thus S/N probably decreases as the lift-off is increased. As a result, it has been acknowledged that a smaller lift-off is more effective in detection of a small target defect.

On the other hand, defects to be measured have a very small concavo-convex level and a large area (corresponding to 5 mm or larger in diameter). Also in detection of such a defect, the defect signal and the noise signal coming from a sample itself decrease together as the lift-off is increased. However, a larger lift-off does not lead to a weaker defect signal because the size of the defect is large and thus the area of the defect encompassed in the detection area of a sensor remains constant until the detection area of the sensor exceeds that of the defect even if the lift-off is increased (see FIG. 11B).

As for noise signals, it can be considered that the random noise component decreases as a result of arithmetic averaging until the lift-off is increased to some extent. Therefore, because of the relationship between the size of the defect and the arithmetic average of random noise, S/N virtually increases until the lift-off reaches a certain value. Further increasing the lift-off would lead to a more significant decrease in the defect signal as with the case of a small defect, thereby probably causing S/N to decrease.

In this way, S/N increases even if the lift-off is increased to some extent as long as the defect is smaller than the area of the sample that can affect the sensor because the increased lift-off reduces noise attributed to the sample itself while keeping the defect signal almost constant. This probably contributes to establishment of the optimum range.

In addition, whetstone inspection usually performed in an iron and steel manufacturing line involves rasping such defects as described above, which each have a concavo-convex level of a few micrometers and a size approximately in the range of 5 to 30 mm in diameter on a steel sheet, with a whetstone to make them visible, but this inspection often further includes inspection of fine defects that can be detected without being rasped with a whetstone. Such defects can be detected without being rasped with a whetstone and thus our method does not handle them.

Figure 12A:
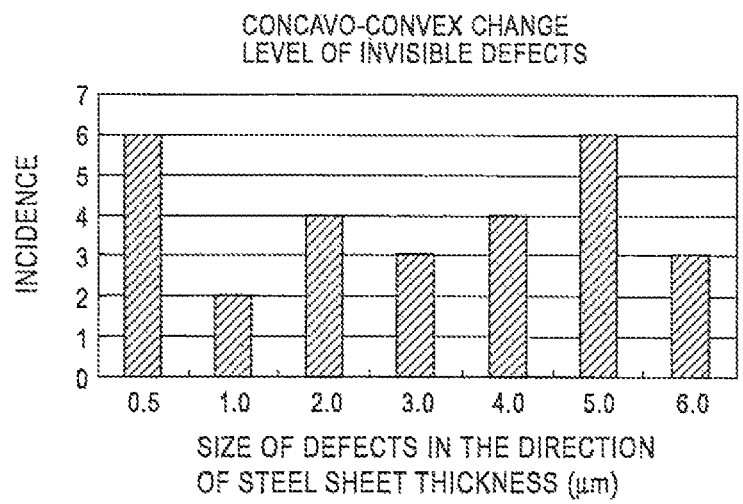
FIGS. 12A and 12B are diagrams each showing the shapes of the sample defects used for evaluation.
Figure 12B:
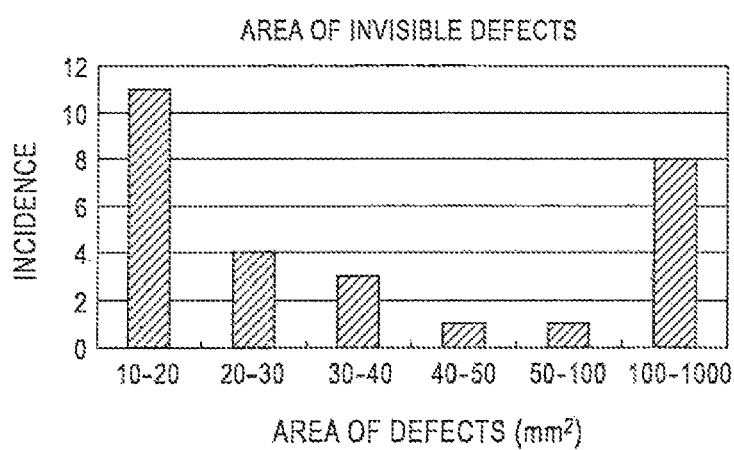

The results based on actual data obtained for defects that are not easily visible (usually almost invisible and detectable only by whetstone inspection) are shown below. FIG. 12 are diagrams each showing the shapes of the sample defects used for evaluation. FIG. 12A is a diagram showing the sizes of almost invisible defects in the direction of steel sheet thickness (concavo-convex change level) and the incidence thereof (the number of samples), whereas FIG. 12B is a diagram showing the areas of the defects on the steel sheet and the incidence thereof (the number of samples).

As shown in FIG. 12, our methods handle fine concavo-convex shape surface defects each having a concavo-convex level (shape change level in the direction of steel sheet thickness) in the range of 0.5 to 6 μm and an area approximately in the range of 10 to 1000 mm² (corresponding to 4 to 30 mm in diameter) on a steel sheet. In addition, these defects existed on steel sheets each having a thickness in the range of 0.4 to 2.3 mm and surface roughness Ra in the range of 0.5 to 2 μm, and the radius of curvature R was 10 mm or larger on the cross-section in the direction of steel sheet thickness.

Figure 13:
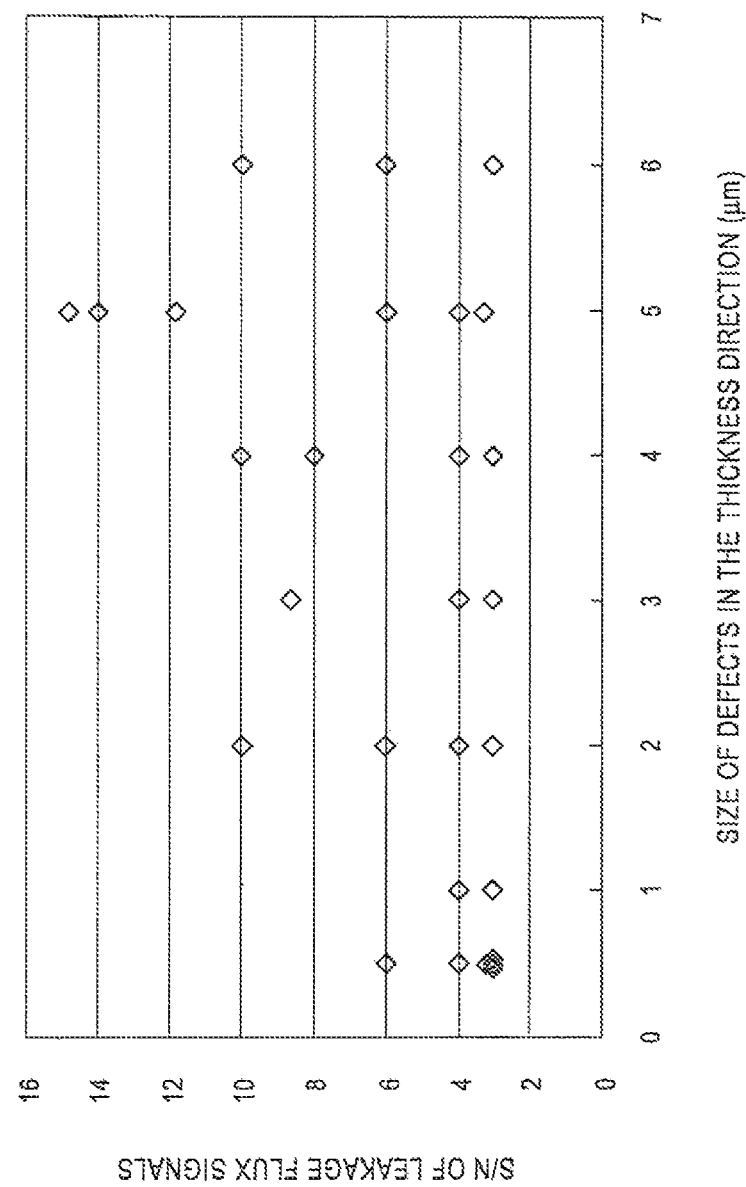
FIG. 13 is a diagram showing the relationship between the size of the defects shown in FIG. 12A in the thickness direction and S/N of leakage flux signals.

Then, FIG. 13 is a diagram showing the relationship between the size of the defects shown in FIG. 12A in the thickness direction and S/N of leakage flux signals. As shown in FIG. 13, S/N of leakage flux signals is 2 or higher for all defects, and this demonstrates that our methods have a sufficient detection sensitivity. It should be noted that, in FIG. 13, four sample defects having a size in the concavo-convex direction (concavo-convex change level) of 0.5 μm showed S/N of approximately 3 and thus the data points for these defects are plotted overlapping each other.

Figure 14:
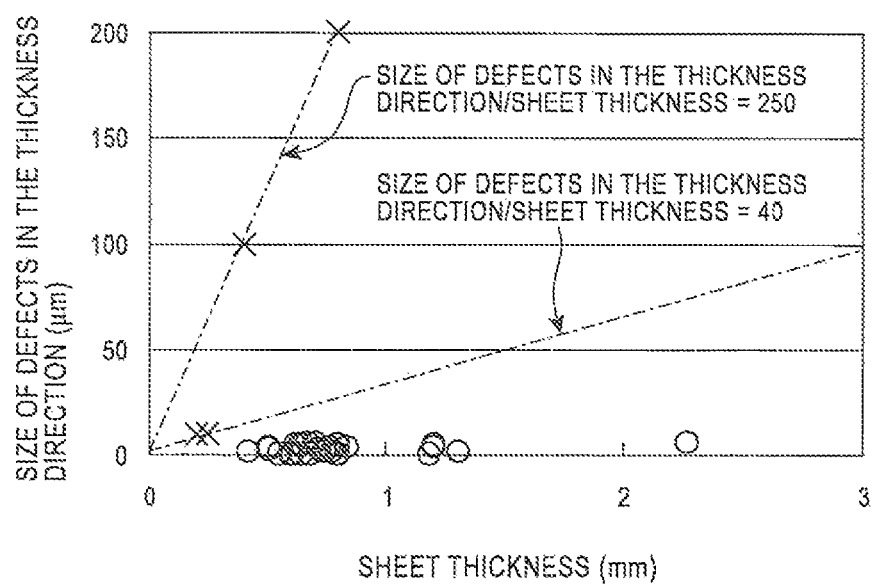
FIG. 14 is a diagram showing the relationship between the size of defects in the thickness direction and the thickness of the test steel sheets.

Furthermore, FIG. 14 is a diagram showing the relationship between the size of defects in the thickness direction and the thickness of the test steel sheets. The data points measured and shown in FIGS. 12 and 13 are represented by ○, and those measured using a known magnetic flux leakage inspection method using a magnetic flux leakage inspection apparatus for steel sheets installed in a line after a cold rolling process are represented by ×. It should be noted that the documents listed earlier showed some data without specifying the sheet thickness and provided only the explanation "intended for steel sheets for cans" for such data, and thus we assumed in plotting such data that the sheet thickness is 0.2 mm, a thickness commonly used for steel sheets for cans.

As can be seen in FIG. 14, the value s/t obtained by dividing the size of a test defect in the thickness direction s (unit: μm) by the thickness of a test sheet t (mm) is large and approximately in the range of 40 to 250 in a known magnetic flux leakage inspection method, whereas the same value is very small, data points obtained in accordance with which are represented by ○. Then, an enlarged view of FIG. 14 with the range of the vertical axis being 0 to 10 μm and the range of the horizontal axis being 0 to 1.5 mm is shown in FIG. 15.

Figure 15:
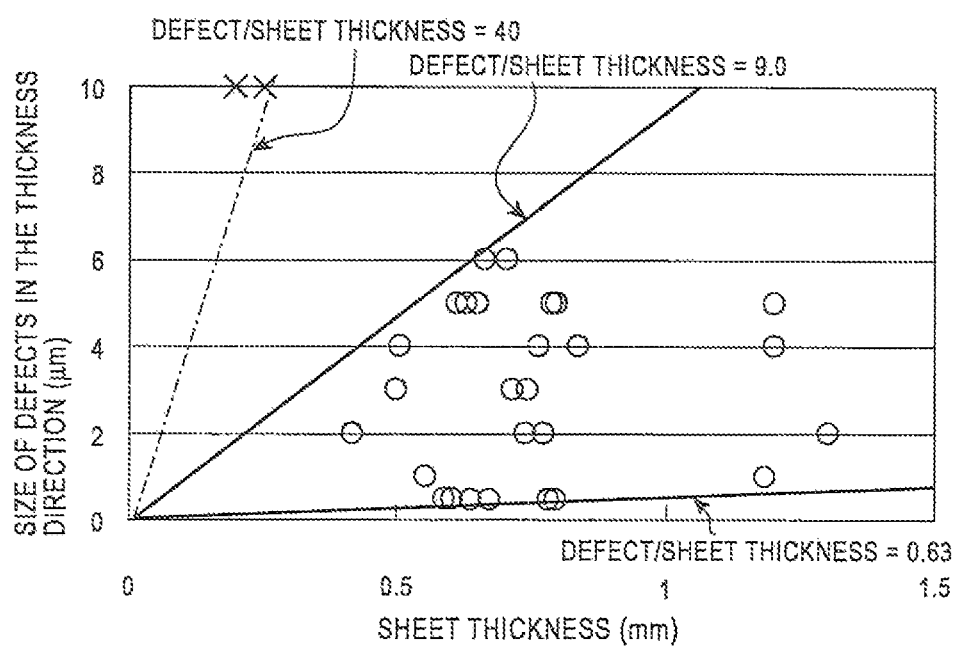
FIG. 15 is an enlarged view of FIG. 14 with the range of the vertical axis being 0 to 10 μm and the range of the horizontal axis being 0 to 1.5 mm.

As shown in FIGS. 13 and 14, our methods handle fine concavo-convex shape surface defects existing on a steel sheet with a thickness in the range of 0.4 to 2.3 mm and each having a concavo-convex level of 0.5 to 6 μm and the value s/t obtained by dividing the size of a defect in the direction of steel sheet thickness s (concavo-convex change level; unit: μm) by the thickness of a test sheet t (mm) is extremely small and in the range of 0.63 to 9.0 as can be seen in FIG. 15. Consequently, it can be concluded that the target of inspection is fine concavo-convex shape surface defects having s/t, the ratio of the size of a defect in the direction of steel sheet thickness s (μm) to the steel sheet thickness (mm), in the range of 0.63 to 9.0.

The invention claimed is:

1. A method for detecting a concavo-convex shape surface defect existing on a ferromagnetic metal object comprising sensing a signal attributed to strain of the concavo-convex shape surface defect having a size in a range of 0.5 to 6 μm.

2. The method according to claim 1, wherein a thickness of the ferromagnetic metal object is in a range of 0.4 to 2.3 mm.

3. The method according to claim 1, wherein a ratio s/t of a size of the concavo-convex shape surface defect in a direction of a thickness s (μm) to the thickness of the ferromagnetic metal object t (mm) is in a range of 0.63 to 9.0.

4. The method according to claim 1, wherein the signal is magnetic flux leaking from the ferromagnetic metal object to which magnetic flux is applied.

5. The method according to claim 4, wherein a magnetic flux density of the ferromagnetic metal object to which the magnetic fax is applied is at least 75% and lower than 95% of the magnetic flux density at magnetic saturation.

6. The method according to claim 4, wherein the sensing is performed under combined conditions including a condition under which the magnetic flux density of the ferromagnetic metal object to which the magnetic flux is applied is at least 75% and lower than 95% of the magnetic flux density at magnetic saturation and another condition under which it is at least 95% of the magnetic flux density at magnetic saturation.

7. The method according to claim 4, wherein an intensity of a magnetic field applied to the ferromagnetic metal object is at least 4000 A/m and less than 25000 A/m.

8. The method according to claim 4, wherein the sensing is performed under a combined condition obtained by combining a condition wider which the intensity of a magnetic field applied to the ferromagnetic metal object is at least 4000 A/m and less than 25000 A/m and another condition under which it is at least 25000 A/m.

9. The method according to claim 1, wherein a distance between the ferromagnetic metal object and a sensing apparatus that senses the signal is in a range of 0.5 to 1.5 mm.

10. The method according to claim 1, wherein the signal is a physical quantity attributed to strain of the concavo-convex shape surface defect occurring in a process that is a process downstream of rolling, which is a cause of the defect, and also is a process upstream of a process producing an annealing effect.

11. The method according to claim 1, wherein the signal is a physical quantity attributed to strain of the concavo-convex shape surface defect occurring in a process that is a process downstream of rolling, which is a cause of the defect, and comes later than temper rolling.

12. A method for detecting a fine concavo-convex shape surface defect that has a concavo-convex level in a range of 0.5 to 6 μm and exists on a ferromagnetic metal sample comprising detecting the surface defect by sensing a signal attributed to strain of a defect portion of the sample.

13. A method for manufacturing a ferromagnetic metal comprising the detection method according to claim 1.

14. A method for manufacturing a ferromagnetic metal comprising the detection method according to claim 10.

15. A method for manufacturing a ferromagnetic metal comprising the detection method according to claim 11.

16. An apparatus for detecting a fine concavo-convex shape surface defect that has a concavo-convex level in a range of 0.5 to 6 μm and exists on a ferromagnetic metal sample comprising a sensor that detects the surface defect by sensing a signal attributed to strain of a defect portion of the sample.

* * * * *